Figure 1:
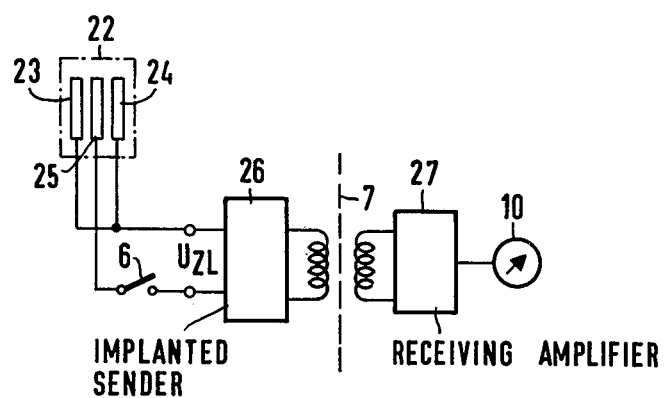

United States Patent [19]

Rao et al.

[11] 4,140,963

[45] Feb. 20, 1979

[54] DEVICE FOR MEASURING SUGAR CONCENTRATION

[75] Inventors: Raghavendra Rao; Ferdinand von Sturm, both of Erlangen, Fed. Rep. of Germany

[73] Assignee: Siemens Aktiengesellschaft, Berlin and Munich, Fed. Rep. of Germany

[21] Appl. No.: 775,186

[22] Filed: Mar. 7, 1977

Related U.S. Application Data

[62] Division of Ser. No. 311,955, Dec. 4, 1972, abandoned.

[30] Foreign Application Priority Data

Jan. 3, 1972 [DE] Fed. Rep. of Germany ....... 2200119

[51] Int. Cl.² .......................................... G01N 27/42
[52] U.S. Cl. ................................. 324/30 R; 324/29.5; 128/419 B; 128/1 R
[58] Field of Search ............... 429/2, 12, 15; 128/2 P, 128/2 E, 2.1 E, 419 B; 324/62, 30 R, 29

[56] References Cited

U.S. PATENT DOCUMENTS 2,181,303   11/1939   Leingang et al. ................... 324/29.5

OTHER PUBLICATIONS

R. F. Drake et al., A Tissue Implantable Fuel Cell Power Supply, vol. XVI, Trans. Amer. Soc. Artif. Int. Organs, 1970, pp. 199-205.

Primary Examiner—M. Tokar
Attorney, Agent, or Firm—Hill, Gross, Simpson, Van Santen, Steadman, Chiara & Simpson

[57] ABSTRACT

A device for measuring sugar concentration, particularly in a body liquid, for example, blood of a patient is characterized in that an electrochemical glucose cell is used to produce an electrical signal corresponding to the sugar concentration.

8 Claims, 3 Drawing Figures

DEVICE FOR MEASURING SUGAR CONCENTRATION

This is a division of application Ser. No. 311,955, filed Dec. 4, 1972, and now abandoned.

This invention relates to a device for measuring sugar concentration, particularly in a body liquid, for example, blood of a patient.

Usually chemical methods are used to determine sugar concentration. The drawback is that when measuring methods are used which can be easily carried out, the results are very inaccurate. Precise results can be obtained only by specialists by hard labor. This drawback is particularly hard for sick persons wherein the blood sugar content must be determined continuously and as precisely as possible in order to be able to apply properly dosed therapy even in case of comparatively quickly varying sugar concentrations. Urine colored examing strips which are offered to diabetics and other sick persons for personally determining their blood sugar produce an extremely inaccurate determination of blood sugar content and therefore cannot be used for precise therapy. The precise determination of blood sugar requiring considerable exertion, takes place by examining patient's blood, so that the patient must come to the hospital or to the doctor. Obviously, due to the trouble to the patient and the resulting costs this cannot be carried out sufficiently often.

An object of the present invention is to provide means for determining sugar concentration which quickly supply a precise measurement and which can be used by technically inexperienced persons. The sick can use the means of the present invention themselves so that they can be continuously informed with sufficient precision about their blood sugar concentration.

Other objects of the present invention will become apparent in the course of the following specification.

In the accomplishment of the objectives of the present invention it was found desirable to use a glucose cell for determining sugar concentration. The glucose cell produces in conjunction with a sugar solution (as electrolyte) an electrical signal which represents a very precise measure for the present sugar concentration value. The signal is produced at once, so that the amount of concentration, if desired, can be read immediately upon a suitable signal indicating device. The use of the cell does not require any special technical experience, so that the amount of concentration can be easily determined by a technically inexperienced person. The cell can be incorporated in the smallest possible space and thus is suitable for being implanted in the body of a patient. This makes it particularly easy for a sick person to be continuously and sufficiently precisely informed about his blood sugar concentration, for example, by a signal indicating device provided close to his body, so that he himself can undertake the corresponding therapeutic measures. The transmission of the appearing electrical signal to the indicating device can take place through electrical conduits extending through the skin or by telemetric means.

The cell can be operated by an outer source of current, for example, a primary cell of mercury oxide zinc type, a secondary cell of gas tight nickel cadmium type, a fuel cell, for example a glucose-oxygen cell, a biogalvanic cell, for example, an aluminum-oxygen cell, or a radio nuclide battery with a thermoelectrical or thermoionic generator. The cell itself can also provide its own current, it may be constructed, for example, as a glucose-oxygen-fuel cell or as a glucose-silver-silverchloride cell.

When the cell is operated from an outer source, it can be supplied with a constant current or a constant voltage. Then the measure for the sugar concentration is the appearing cell voltage or cell current. The cell can be also connected for a short time to a source of constant current and then the measured transition time period of the cell voltage will be a measure for the concentration.

When the cell is operated by its own current the measure for the concentration can be either the idle voltage of the cell or the cell current or cell voltage for a high ohmic loaded cell. The transition time period can be equally well determined by bridging the cell for a short time by a low ohmic resistance.

The invention will appear more clearly from the following detailed description when taken in connection with the accompanying drawings showing by way of example only, preferred embodiments of the inventive idea.

Figure 2:
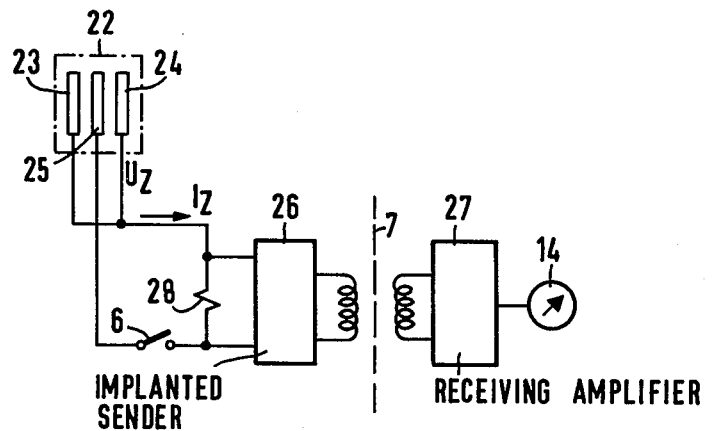
Figure 3:
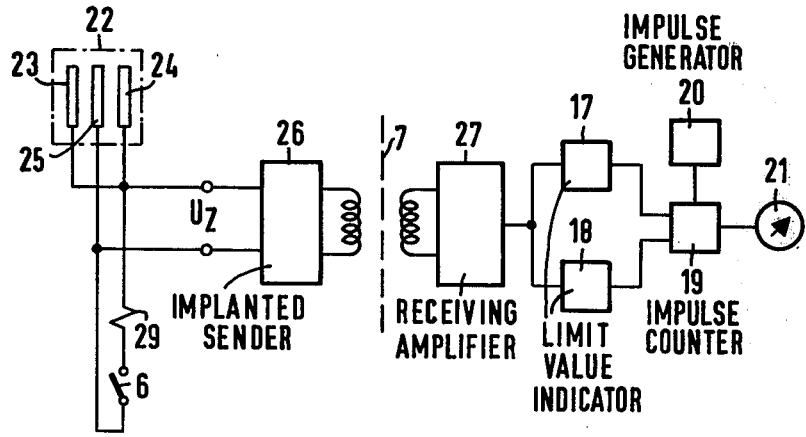

In the drawings:

Each of the FIGS. 1 to 3 is a circuit diagram of a different embodiment of a device of the present invention.

In the embodiments shown in FIGS. 1, 2 and 3 current providing glucose-oxygen cells 22 are used as glucose cells. Each of these cells 22 consists of two oxygen electrodes 23, 24 which transmit glucose and a glucose electrode 25 located between the oxygen electrodes. The electrodes are separated from each other and from the body liquid by separating walls of a hydrophilic material, preferably an ion exchanger. The oxygen electrodes 23, 24 consist of a silver net with carbon applied as a catalyst. The glucose electrode 25 consists of platinized platinum. The surface of each electrode amounts to 6.3 $cm^2$.

The transmission of electrical signals supplied by the cells 22 through the skin 7 of the patient takes place here telemetrically in the usual manner by the use of an implanted sender 26 as well as a receiving amplifier 27.

In the embodiment of FIG. 1 the line idle voltage $U_{ZL}$ produced after the closing of the switch 6 is transmitted and is shown in an indicating device 10.

In the embodiment of FIG. 2 the cell 22 is loaded with a high ohmic resistance 28, for example, 20 k ohm and the created cell current $I_Z$ is measured as a measure for glucose concentration.

In the embodiment of FIG. 3 the cell 22 can be connected with a low ohmic resistance 29, preferably 200 ohm. Then the time run of the cell voltage $U_Z$ is transmitted, and the transition time is determined and indicated by a corresponding circuit consisting of parts 17 to 21.

In this embodiment the time flow of the voltage $U_Z$ is examined when the switch 6 is closed. The voltage $U_Z$ is transmitted to receiving amplifier 27 and limit value indicators 17 and 18 connected behind the amplifier. The indicator 17 produces an outgoing signal as soon as the voltage $U_Z$ exceeds a fixed value which is preferably somewhat below the first transition potential stage of the cell. The indicator 18 produces an outgoing signal when the voltage $U_Z$ exceeds a specific value a little above the potential stage.

The outgoing signal of the indicator 17 starts an impulse counter 19 which counts the outgoing impulses of an impulse producer 20 (it can be switched on, for example, by the closing signal for the switch 6). The outgoing signal of the indicator 18 stops the counter 19.

The number of pulses of the impulse producer 20 counted by the counter 19 is a measure for the transition time period of the cell voltage $U_Z$ at the corresponding potential stage. The duration of the transition is again a measure for the glucose concentration. An indicating instrument 21 connected behind the counter 19 shows directly the glucose concentration value.

What is claimed is:

1. Apparatus for measuring sugar concentration of human blood, comprising a cell (22) combining an electrode (25) composed of platinized platinum as the glucose electrode with at least one carbon catalyst electrode (23, 24) permeable to glucose, as the oxygen electrode, and a current sensing means coupled to said cell (22), the cell (22) itself is constructed so as to supply current to the current sensing means coupled to said cell (22) for providing an accurate measure of said sugar concentration.

2. Apparatus according to claim 1 with the cell (22) providing a cell idle voltage ($U_{ZL}$), said current sensing means comprising a volt meter (26, 27, 10) for determining the cell idle voltage ($U_{ZL}$) connected to the electrodes (25, 23, 24) of the cell (22).

3. Apparatus according to claim 1, with the electrodes (25, 23, 24) of the cell (22) being loaded with a resistance (28) of at least about twenty kilohms, and said current sensing means comprising a meter (26 through 28) selectively connected to the electrodes.

4. Apparatus according to claim 1, with a switch (6) connecting the electrodes (25, 23, 24) of the cell (22) to a resistance (29) of not more than about two hundred ohms, said current sensing means comprising a volt meter with a limit value indicator (17, 18) connected to the electrodes for sensing a transition time period of the cell voltage.

5. Apparatus for measuring sugar concentration of human blood, comprising a cell (22) combining a glucose-electrode composed of platinum with at least one counter electrode composed of silver/silverchloride, a current sensing means coupled to said cell (22), the cell (22) itself is constructed so as to supply current to the current sensing means for providing an accurate measure of said sugar concentration.

6. Apparatus according to claim 5, with the cell providing a cell idle voltage ($U_{ZL}$), said current sensing means comprising a volt meter (26, 27, 10) for determining the cell idle voltage ($U_{ZL}$) connected to the electrodes (25, 23, 24) of said cell (22).

7. Apparatus according to claim 5, with the electrodes (25, 23, 24) of the cell (22) being loaded with a resistance (28) of at least about twenty kilohms, and said current sensing means comprising a meter (26 through 28) selectively connected to the electrodes.

8. Apparatus according to claim 5, with a switch (6) connecting the electrodes (25, 23, 24) of the cell (22) to a resistance (29) of not more than about two hundred ohms, said current sensing means comprising a volt meter with a limit value indicator (17, 18) connected to the electrodes for sensing a transition time period of the cell voltage.

* * * * *